United States Patent [19]

Lapins et al.

[11] Patent Number: 4,933,284
[45] Date of Patent: Jun. 12, 1990

[54] REGENERABLE DIALKYLAMINOALKYL CELLULOSE SUPPORT MATRIX FOR IMMOBILIZING BIOLOGICALLY ACTIVE MATERIALS

[75] Inventors: Chris D. Lapins, Cicero; Yoshihisa Tsuda, Wilmette, both of Ill.

[73] Assignee: UOP, Des Plaines, Ill.

[21] Appl. No.: 246,101

[22] Filed: Sep. 19, 1988

Related U.S. Application Data

[63] Continuation-in-part of Ser. No. 860,398, May 7, 1986, abandoned.

[51] Int. Cl.$^5$ .................. C12N 11/14; C12N 11/12; G01N 33/548; C07K 17/12
[52] U.S. Cl. .................. 435/176; 435/179; 436/524; 436/530; 530/811; 530/814; 536/63; 536/69; 536/84; 536/99
[58] Field of Search .................. 435/94, 176, 179; 436/524, 530; 530/811, 814; 536/32, 43, 63, 69, 84, 99

[56] References Cited

U.S. PATENT DOCUMENTS

| | | | |
|---|---|---|---|
| 3,251,824 | 5/1966 | Battista | 536/99 X |
| 3,823,133 | 7/1974 | Hurst et al. | 435/179 X |
| 3,905,954 | 9/1975 | Jones et al. | 435/179 X |
| 4,048,018 | 9/1977 | Coughlin et al. | 435/176 |
| 4,141,857 | 2/1979 | Levy et al. | 252/430 |
| 4,248,969 | 2/1981 | Lee | 435/176 |
| 4,250,260 | 2/1981 | Rohrbach et al. | 435/176 |
| 4,343,902 | 8/1982 | Ushiro | 435/94 |

OTHER PUBLICATIONS

Kirk-Othmer, "Encyclopedia of Chemical Technology", Third Ed., vol. 9, pp. 155–157.

*Primary Examiner*—David M. Naff
*Attorney, Agent, or Firm*—Thomas K. McBride; Eugene I. Snyder

[57] ABSTRACT

A regenerable support matrix useful for immobilization of biologically active materials is prepared by coating a core support with a cellulose ester, removing ester groups by hydrolysis to produce hydroxyl groups and converting the hydroxyl groups to dialkylaminoalkyl ether groups. The support matrix can immobilize biologically active proteinaceous materials with a net negative charge by adsorption. The support matrix is readily regenerated when an immobilized biologically active material becomes inactive by washing the support with a base or salt solution and adsorbing additional biologically active material to the support. Multiple cycles of immobilization and regeneration are possible without significant deleterious affects.

12 Claims, No Drawings

4,933,284

REGENERABLE DIALKYLAMINOALKYL CELLULOSE SUPPORT MATRIX FOR IMMOBILIZING BIOLOGICALLY ACTIVE MATERIALS

CROSS REFERENCE TO RELATED APPLICATIONS

This application is a continuation-in-part of my copending application, Ser. No. 860,398, filed May 7, 1986, now abandoned all of which is hereby incorporated by reference.

BACKGROUND OF THE INVENTION

Methods for the immobilization of biologically active materials, especially enzymes, have undergone such rapid development in recent years that it is fair to say that support matrices and their preparation are rather mature fields of knowledge in, for example, enzyme catalyzed reactions of commercial importance. The impetus for their development initially was the conservation of enzymes; the use of enzymes in homogeneous reactions generally mandated the single use of enzymes. Because enzymes often are an expensive, and perhaps the most expensive, component of reactions there arose the need to develop methods allowing multiple use of enzymes. Immobilization of enzymes on solid supports led to heterogeneous enzyme-catalyzed reactions where the immobilized enzymes could be readily removed, as in a stirred batch reactor, or could be employed in a continuous process, as in a fixed bed, but in either case permitted enzyme-catalyzed processes where the enzyme could be reused until its decreased activity made further use economically unfeasible.

Presently there are a variety of support matrices from which immobilized enzymes specifically, and immobilized biologically active materials generally, can be prepared. Some bind the enzyme, as exemplary of a biologically active material, via ionic interaction, others bind the enzyme via entrapment. In still others the biologically active material is immobilized by covalent bonding to the support or some intermediary linked to the support. Thus, the skilled worker has some realistic alternatives in his technological closet when seeking a support matrix with which to immobilize a biologically active substance.

Nonetheless, there remains some technologically significant gaps in the field of support matrices. One highly desirable goal is the preparation of a support matrix which is conveniently and cheaply regenerable when the activity of its immobilized biologically active material strips it of economic benefit. It is even more preferable that the support matrix could be regenerated multiple times, with its subsequent activity in immobilizing biological material undiminished. Some limited success has been achieved, as e.g., the methods taught in U.S. Pat. Nos. 4,248,969 and 4,250,260, but even more economical systems are greatly desired.

Among the supports that have been used to immobilize enzymes is included diethylaminoethyl cellulose (DEAE-cellulose), a support material chosen because of its relatively low cost but whose use is largely limited to a stirred tank reactor. Kirk-Othmer, "Encyclopedia of Chemical Technology" Third Edition, V. 9, p. 155 (J. Wiley & Sons, 1980). Such a support material is unsuitable for use in a packed bed reactor because of its poor flow characteristics, one of the required characteristics necessary for use in a packed bed. In fact, DEAE-cellulose appears to have been used in the first commercial process in the United States using immobilized glucose isomerase (op. cit., p. 157), although it was soon succeeded by other immobilized glucose isomerase systems which could be used as a packed bed.

To attain the good flow necessary for a continuous process in a packed bed reactor it is desirable for the particles to be incompressible, hard, unreactive materials, as are the refractory inorganic oxides such as alumina, silica, glass, and so forth, and ceramics. In fact, the latter materials are core materials in supports where they are coated with an organic resin which binds to the biologically active materials, as exemplified by U.S. Pat. No. 4,141,857.

This application describes a support matrix having all the characteristics necessary for its successful use in a packed bed, but with the additional characteristic of being readily regenerable from an exhausted or deactivated enzyme immobilized thereon. The support matrix of this invention is easy to make, economical, immobilizes a broad variety of biologically active materials, and is regenerable using extraordinarily simple and rapid means.

SUMMARY OF THE INVENTION

The purpose of this invention is to prepare a support matrix useful for the immobilization of biologically active materials and which can be readily regenerated when the activity of the immobilized biologically active material is reduced below some desired level. An embodiment comprises a core support of a refractory inorganic oxide coated with cellulose whose hydroxyl groups are partially converted to dialkylaminoalkyl ether derivatives. In a more specific embodiment the cellulose is DEAE-cellulose. In a still more specific embodiment the oxide is alumina.

DESCRIPTION OF THE INVENTION

The support matrix of this invention can be viewed, at least conceptually, as being composed of several functionally related parts. At the heart of the matrix is the core support, generally a relatively incompressible, abrasion-resistant solid chemically inert under typical enzymatic process conditions, and whose packed bed exhibits good flow characteristics. The core support is coated with cellulose whose hydroxyl groups are partially derivatized to form dialkylaminoalkyl ethers of cellulose. The resulting support matrix is able to immobilize many enzymes via strong ion exchange forces. Although the enzymes remain bound to the support matrix without substantial leaching under reaction conditions typical of enzyme-catalyzed reactions, the spend enzyme is readily removed from the matrix by washing with base or a concentrated salt solution, thereby regenerating the support matrix. Many cycles of enzyme immobilization-support matrix regeneration are possible with virtually no deleterious effects.

The core supports which may be used in the practice of this invention are best characterized functionally. Thus, they are incompressible materials, totally inert under reaction conditions typical of enzymatic reactions, and are tough, abrasion resistant particles which when packed in a bed show good flow characteristics. Any material which has these functional characteristics may be used in the practice of this invention. Examples include the refractory inorganic oxides, glass, especially porous glass, and ceramic materials. Among the refractory inorganic oxides may be mentioned aluminum oxide, silicon oxide, thorium oxide, zirconium oxide, magnesium oxide, titanium oxide, and combinations thereof. Aluminum oxide is an especially desirable core support.

The core support is then coated with cellulose. Because of the insolubility of cellulose itself in most solvents, the core support generally is not directly coated with cellulose, but rather with a soluble derivative of cellulose which can be readily converted, as by hydrolysis, to cellulose itself. Any cellulose derivative which is soluble in a low boiling organic solvent and which can be readily converted chemically to cellulose may be used in the practice of this invention. Cellulose esters as a group are good cellulose derivatives to use in the practice of this invention, and the use of cellulose acetate is especially convenient. Although the following description will be couched in terms of cellulose acetate it needs to be recognized that the acetate is used solely in a representative capacity.

To coat the core support a solution of cellulose acetate, for example, in an organic solvent is contacted with the core support. One method of coating the core support is to mix the latter with a solution of cellulose acetate in an amount sufficient to afford the weight of cellulose acetate which is desired to be coated on the core support, and gradually evaporating the organic solvent. In this mode of coating the core support in particular a relatively low boiling organic solvent, i.e., one whose boiling point is under about 100° C., is desired to facilitate subsequent removal of the organic solvent. However, it is to be recognized that this is only a convenience feature, and the boiling point of the organic solvent is not critical to the success of this invention.

Another general method of coating the core support with cellulose acetate is to recycle an organic solution of the acetate through a bed of the core support. With continued recycling the core support generally absorbs an equilibrium amount of cellulose acetate, the amount depending somewhat upon the concentration of cellulose acetate in the solution, the nature of the organic solvent, and the support absorbing the acetate from solution. When equilibrium is attained excess solution is drained from the column and the organic solvent is removed, such as by evaporation with heat or in a gas stream.

The cellulose acetate-coated core support is then reacted so as to remove virtually all of the acetate groups. Hydrolysis in the presence of base is particularly useful, and can be done by methods well known in the art. For example, the cellulose acetate-coated core support may be reacted with a solution of an alkai at a concentration from about 0.5% to about 4% (W/V) at a temperature from about 25° C. to about 70°C. It needs to be understood that many hydrolytic methods are known in the art and need not be further exemplified here. What is important, as will be readily appreciated by those skilled in the art, is that the base, its concentration, the reaction temperature and time have no effect on the core support or on the cellulose acetate-coated thereon other than to hydrolyze the acetate ester linkage. Using such hydrolytic methods at least about 80% of the ester groups are removed, and generally more than about 90% will be so removed.

It is desired that from about 1% to about 20% by weight of the finished material be cellulose, as calculated on a dry basis. It has been found that a cellulose content of greater than about 15% by weight confers no additional benefit in the practice of this invention, and a cellulose-coated core support containing from about 1% to about 10% by weight of cellulose as calculated on dry weight of finished product is preferred.

The free hydroxyl groups of the cellulose coated core support as prepared above are then converted to a dialkylaminoalkyl ether of cellulose. Methods therefor, based on reaction of the free hydroxyl groups with a dialkylaminoalkyl halide, also are well known and are exemplified by reaction of the cellulose coated core support with a solution of the dialkylaminoalkyl chloride hydrochloride in the presence of base for a time between about 1 and 10 hours at a temperature between about 30° and 80°C.

The dialkylaminoalkyl portion of the cellulose ethers prepared have the formula $R_aR_bN(CH_2)_p-$, where $R_a$ and $R_b$ are independently selected from the group consisting of saturated alkyl moieties, $C_nH_{2n+1}$, where n is an integer from 1 to 20, usually from 1 to 6, and even more often is from 1 through 4. The alkyl groups which may be used in the practice of this invention include methyl, ethyl, propyl, butyl, pentyl, hexyl, heptyl, octyl, nonyl, decyl, undecyl, dodecyl, tetradecyl, pentadecyl, hexadecyl, heptadecyl, octadecyl, nonadecyl, and eicosyl groups. Primary alkyl groups are especially preferred to minimize effects arising from steric hindrance, and the use of diethylaminoalkyl ethers is especially preferred.

The size of the methylene chain may vary between ethylene ($p=2$) through about decylene ($p=10$), with a size where p is 2, 3, or 4 being especially preferred, and the ethylene moiety ($p=2$) being especially desirable. The diethylaminoethyl ethers, where both $R_a$, $R_b$, and $(CH_2)_p$ are 2-carbon fragments, are especially desirable in the practice of this invention.

It is not possible, nor is it necessarily desirable, to convert all the hydroxyl groups of the cellulose coated core support to the corresponding dialkylaminoalkyl ethers. Generally an extent of derivatization sufficient to afford between 0.2 and about 2.0 milliequivalents of ether groups per gram of dry finished support matrix is desirable, with the range between about 0.5 to about 1.2 meq/g being the most common extent of derivatization.

At this stage the support matrix is complete. It now can be used to immobilize biologically active materials, such as enzymes, cofactors, antibodies, antigens, and proteinaceous materials generally. Because of the nature of the support matrix the active biological material needs to be of the appropriate charge type. That is, the support matrices of this invention act like anion exchangers in immobilizing biological materials. Therefore, biologically active materials which have at least a small excess of negative charge are most effectively immobilized in the practice of this invention. Immobilization can be effected simply by first washing the support matrix with a buffer at a suitable pH, generally in the range between 5.5 and about 8.5, followed by mixing a solution of the biologically active material, such as an enzyme, in a buffer at the same pH as was used for washing for a time sufficient to achieve equilibrium, generally from about 5 to about 20 hours. Excess solution containing biological material is then removed, as by draining, and the immobilized biologically active material is then washed well with water to remove adhering biologically active substance which normally would readily be removed by leaching in the early stages of any process where it was used continuously in a packed bed. Immobilization generally is done at a temperature under about 40° C., more usually under about 25° C., and often at a temperature between about 5° and about 20° C.

As previously stated, any biologically active materials of appropriate net charge type may be immobilized by the practice of this invention. Thus, enzymes, cofactors, antibodies, antigens, and other proteinaceous materials which have a net negative charge, i.e., an isoelectric point greater than 7.0, can be immobilized by the support matrices described herein, although not all are necessarily immobilized to the same extent or with the same efficiency. Examples of several enzymes which may be used in the practice of this invention, which are illustrative only, include glucose isomerase, invertase, penicillin acylase, naringase, dextran sucrase, and ATP deamidase.

An important and outstanding feature of the support matrices herein is their facile regeneration when the biological material immobilized thereon has been deactivated, or is no longer desired to be used for any other reason. Regeneration of the support matrix is readily accomplished by contacting the immobilized system with a solution of dilute base or with a concentrated salt solution.

Among the bases which may be used are the alkali metal hydroxides, such as sodium hydroxide, potassium hydroxide, and lithium hydroxide; alkaline earth hydroxides such a barrium hydroxide, calcium hydroxide, and magnesium hydroxide; and ammonium hydroxide and quaternary ammonium hydroxides. Concentrations of the base which degrade the underlying core support place upper limitations on base concentration; e.g. when using the alkali metal hydroxides with a system whose core support is alumina, a concentration in excess of about 1 N is to be avoided. Although an aqueous solution as dilute as 0.02 N may be used, solutions of base between about 0.1 and 1.0 N are more typical. Base volumes from 10-15 times that of the immobilized system suffice, although a volume as low as 2-3 times may be used with sufficiently concentrated base solutions and perhaps extended contact time, with regeneration times generally no longer than 30 minutes being required at ambient temperature. Where salt solutions are used for regenerations concentrations of 2-3 molar suffice for highly ionic species such as sodium chloride, potassium chloride, ammonium chloride, ammonium sulfate, sodium sulfate, and so forth. The nature of the salt is relatively unimportant so long as it is unreactive with the core support, is highly dissociated in aqueous solution, and is sufficiently soluble in water to give a solution whose ionic strength is at least that of a 2 M solution of sodium chloride. Whether base or salt is used to treat the immobilized biologically active system, the excess of base or salt is subsequently removed by washing the treated system with copious quantities of water or a buffer at or near a neutral pH, between 5.5 and 8.5. Treatment of the deactivated immobilized system according to the aforegoing description then regenerates a support matrix which can be used to immobilize fresh or different immobilized biologically active material. Many such cycles of regeneration are possible without significant effect on the resulting immobilized biologically active material or on the support matrix itself.

The examples below are merely illustrative of this invention which is not to be limited thereby.

EXAMPLE 1

Cellulose-coated gamma-alumina. Gamma-alumina (30 g, approximately 100 cc), dried at 105° C. overnight, was loaded into a jacketed column (3.0×50 cm). Acetone solutions (300 ml) of various concentrations of cellulose acetate (acetate content ca. 28%) were pumped upflow through the column, and a vibrator was used to aid in fluidizing the alumina. The system was left on recycle for 1 hour after which the acetone solution was drained downflow using a pump. The coated base was dried with a stream of nitrogen gas upflow for 2 hours with water at 60° C. being circulated through the jacket.

The resulting cellulose acetate-coated base was treated with 300 ml of a solution containing 6 g of sodium hydroxide at 60° C. to hydrolyze the acetate. After reaction was complete (2 hours), the cellulose coated base was washed with deionized water until the pH of the wash solution reached neutrality. The cellulose content of the coated bases was determined as loss of ignition at 900° C. and values are summarized in Table 1.

TABLE 1

| Cellulose Content of the Supports | | |
|---|---|---|
| Cellulose Acetate Offered per 30 g Alumina Base | Loss on Ignition Cellulose Content, % | GI Activity after Immobilzation, μ/g |
| 6.0 | 6.9 | 1475 |
| 9.0 | 10.2 | 1480 |
| 12.0 | 13.7 | 1560 |

All cellulose-coated base (30 g) was treated with 9 g of diethylaminoethyl chloride hydrochloride to immobilize glucose isomerase.

Preparation of DEAE-cellulose coated alumina base.

Alumina base (30 g) coated with 10% cellulose was fluidized in the jacketed column described above using 300 ml of solution containing 3 g sodium hydroxide and varying amounts of diethylaminoethyl chloride hydrochloride. The solution was recycled upflow for 4–5 hours at 60° C. After this time spent solution was drained downflow from the column, and the base was washed with deionized water until the effluent had a pH of 7.5-8.0.

Preparation of Immobilized glucose isomerase. To 30 g of DEAE-cellulose-coated alumina base as prepared in the prior example was passed upflow 500 ml of 0.2 M imidazole hydrochloride buffer at pH 7.2. Excess buffer was then washed off the base with deionized water, and water was drained. Glucose isomerase was diluted with 0.05 M imidazole buffer at pH 7.2 with the final enzyme solution at 500 ml. The enzyme solution was recycled upflow to the column for a period from 16 to 20 hours. Table 2 shows the activity of the resulting immobilized glucose isomerase when the offering solution contained the enzyme at levels between 1100 to 3200 units per gram and the base contained 10.2% cellulose, 30 g of which were treated with 3.0 g of diethylaminoethyl chloride hydrochloride. The enzyme solution and the support were fluidized in the column at 60° C. Liquid was removed from the column and unbonded enzyme was removed by washing the immobilized enzyme system with water.

TABLE 2

Immobilization of Glucose Isomerase to DEAE-Cellulose-Coated Alumina Base

| Enzyme Offering, u/g | Initial Activity of IMGi, μ/g |
|---|---|
| 1100 | 620 |
| 1600 | 990 |
| 2500 | 1180 |
| 3200 | 1420 |

The results of immobilizing GI on a cellulose-coated base (10 weight percent cellulose) treated with varying amounts of diethylaminoethyl chloride hydrochloride are summarized in Table 3.

TABLE 3

Effect of Diethylaminoethyl Chloride Hydrochloride Concentration in Preparation of DEAE-Cellulose Coated Alumina.

| Diethylaminoethyl Chloride Hydrochloride Offered per 30 g Base | GI Activity, μ/g |
|---|---|
| 3.0 | 1740 |
| 4.5 | 1470 |
| 6.0 | 1460 |
| 4.0 | 1350 |

Half life of immobilized glucose isomerase. The thermal stability of immobilized glucose isomerase was determined at 60° and 65° C. using 15 cc of immobilized glucose isomerase, as prepared above, in a water jacketed column used as an integral reactor. The feedstock contained 45% (w/w) glucose, $10^{3 1\; 3}$ M $MgCl_2$ and 1000 ppm $Na_2SO_3$, pH 8.0 adjusted with sodium hydroxide. The feed was pumped downflow through the reactor and the flow rate was adjusted to maintain 42% fructose in the product. Samples from the reactor were collected and both glucose and fructose concentrations were determined by high pressure liquid chromatography. At 60° C. the half life was about 90 days, and at 65° C. the half life was about 35 days.

Stripping and reimmobilization of glucose isomerase. Glucose isomerase immobilized on the DEAE-cellulose coated alumina was removed by washing the spent enzyme with sodium hydroxide solution (0.5 N) or a salt solution (NaCl or KCl, 2 M) and the same base was reused for subsequent immobilization of enzyme. Glucose isomerase was immobilized as described above. For example, glucose isomerase was removed by washing the catalyst with 0.5 N sodium hydroxide at room temperature. The stripped support was washed with water and equilibrated with imidazole buffer, pH 7.2. Glucose isomerase was offered (3200 u/g) to the regenerated support matrix as described previously. No significant decline in the capacity of the immobilization of glucose isomerase was observed up to three regenerations, as shown in Table 4. A support matrix regenerated from an IMGI having a half-life of 92 days at 60° C. was used to prepare another IMGI, whose half-life was experimentally indistinguishable from its predecessor.

TABLE 4

Stripping and Reimmobilization of Glucose Isomerase.

| Immobilization | Stripping | Activity, u/g |
|---|---|---|
| 1 | 0 | 1910 |
| 2 | 1 | 2000 |
| 3 | 2 | 1860 |
| 4 | 3 | 1820 |

EXAMPLE 2

Immobilization of invertase. Immobilization of invertase to DEAE-cellulose alumina base was similar to the immobilization of glucose isomerase. Invertase was offered at a level of 13,000 units per gram of base, and 8200 units per gram of the enzyme activity was expressed after immobilization. Thermal stability of the catalyst was evaluated at 50° C., pH 5.5, using 60% (w/w) sucrose as the feed in the presence of 500 ppm $Na_2SO_3$. The catalyst showed no sign of thermal deactivation after more than twelve days on stream.

What is claimed is:

1. A method of immobilizing biologically active material on a support matrix and regenerating the support matrix from subsequently deactivated biologically active material consisting essentially of coating a core support with a cellulose ester, removing by hydrolysis at least about 80% of the ester groups to provide free hydroxyl groups, converting said hydroxyl groups to dialkylaminoalkyl ether moieties, said dialkylaminoalkyl moiety having the formula $R_aR_bN(CH_2)_p-$, where $R_a$, $R_b$ are independently selected from the group consisting of alkyl groups of the formula $C_nH_{2n+1}$, with n being an integer from 1 to about 20, and p being an integer from 2 to about 10, to afford a support matrix, contacting the support matrix with a solution of biologically active material having net negative charge under immobilizing conditions to absorb the biologically active material onto the support matrix by ion exchange forces to afford an active immobilized biological material system, using the active immobilized biological material system to catalyze a reaction whereby the immobilized biological material system becomes inactive, contacting the subsequently deactivated immobilized biological material system with an aqueous solution of a base or highly dissociated salt at a concentration, a temperature, and for a time sufficient to remove the deactivated biological material immobilized thereon, removing excess base or salt by washing with water or a buffer solution contacting the washed support matrix with a solution of the biologically active material to produce a regenerated support matrix containing the biologically active material, and recovering the regenerated support matrix.

2. The method of claim 1 where coating is effected by contacting the core support with a solution of a cellulose ester in an organic solvent whose boiling point is less than about 100° C.

3. The method of claim 1 where the core support is a refractory inorganic oxide, glass, or a ceramic material.

4. The method of claim 3 where the oxide is selected from the group consisting of aluminum oxide, silicon oxide, thorium oxide, zirconium oxide, titanium oxide, magnesium oxide, and combinations thereof.

5. The method of claim 4 where the oxide is aluminum oxide.

6. The method of claim 1 where hydrolysis is effected by reacting the cellulose ester on the core support with a solution of an alkali at a concentration from about 0.5 to about 4 weight-volume percent at a temperature from about 25° to about 70° C.

7. The method of claim 1 where converting the hydroxyl groups is effected by reacting said groups with a dialkylamino-alkyl halide.

8. The method of claim 1 where $R_a$, $R_b$ are lower alkyl groups having 1 to 6 carbon atoms.

9. The method of claim 1 where p is an integer from 2 to about 4.

10. The method of claim 9 where p is 2.

11. The method of claim 1 where the biologically active material is proteinaceous material whose isoelectric point is greater than about 7.0.

12. The method of claim 1 where the material is an enzyme, a cofactor, an antibody, or an antigen.

* * * * *